United States Patent
Feild

(10) Patent No.: US 6,350,858 B1
(45) Date of Patent: Feb. 26, 2002

(54) HUMAN SODIUM DEPENDENT PHOSPHATE TRANSPORTER (IPT-1)

(75) Inventor: John Feild, Wayne, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/553,132

(22) Filed: Apr. 19, 2000

Related U.S. Application Data

(62) Division of application No. 08/935,433, filed on Sep. 23, 1997.
(60) Provisional application No. 60/044,974, filed on Apr. 28, 1997.

(51) Int. Cl.⁷ .................................................. C07K 1/00
(52) U.S. Cl. ........................................................ 530/350
(58) Field of Search ......................................... 530/350

(56) References Cited

U.S. PATENT DOCUMENTS

| | | | |
|---|---|---|---|
| 5,508,164 A | | 4/1996 | Kausch et al. |
| 5,618,677 A | * | 4/1997 | Ni et al. |

FOREIGN PATENT DOCUMENTS

| | | |
|---|---|---|
| WO | WO 96/34288 | 10/1996 |

OTHER PUBLICATIONS

EST 1756454.

Helps, C. et al., "Cloning, sequence analysis and expression of the cDNA encoding a sodium–dependent phosphate transporter from the bovine renal epithelial cell line NBL–1", Eur. J. Biochem. 228, 927–930 (1995).

Ni, B., et al., "Molecular Cloning, Expression, and Chromosomal Localization of a Human Brain–$Na^+$–Dependent Inorganic Phosphate Cotransporter", 66, 2227–2238 (1996).

George, et al., "Current Methods in Sequence Comparison and Analysis", Macromolecular Sequencing and Synthesis, pp. 127–149 (1988).

* cited by examiner

Primary Examiner—Michael Pak
(74) Attorney, Agent, or Firm—William T. Han; Ratner & Prestia; William T. King

(57) ABSTRACT

IPT-1 polypeptides and polynucleotides and methods for producing such polypeptides by recombinant techniques are disclosed. Also disclosed are methods for utilizing IPT-1 polypeptides and polynucleotides in the design of protocols for the treatment of chronic renal failure, end stage renal disease, uremic bone disease, and cancer, among others, and diagnostic assays for such conditions.

2 Claims, No Drawings

SEQUENCE LISTING

<160> NUMBER OF SEQ ID NOS: 4

<210> SEQ ID NO 1
<211> LENGTH: 2288
<212> TYPE: DNA
<213> ORGANISM: HOMO SAPIENS

<400> SEQUENCE: 1

```
cgggccaggt ttccaggctc ggccgccgcc tccatcccag cacctgcgga gggagcgctg      60
accatggctc cctggcctga attgggagat gcccagccca accccgataa gtacctcgaa     120
ggggccgcag gtcagcagcc cactgcccct gataaaagca aagagaccaa caaaacagat     180
aacactgagg cacctgtaac caagattgaa cttctgccgt cctactccac ggctacactg     240
atagatgagc ccactgaggt ggatgacccc tggaacctac ccactcttca ggactcgggg     300
atcaagtggt cagagagaga caccaaaggg aagattctct gtttcttcca agggattggg     360
agattgattt tacttctcgg atttctctac tttttcgtgt gctccctgga tattcttagt     420
agcgccttcc agctggttgg aggaaaaatg gcaggacagt tcttcagcaa cagctctatt     480
atgtccaacc ctttgttggg gctggtgatc ggggtgctgg tgaccgtctt ggtgcagagc     540
tccagcacct caacgtccat cgttgtcagc atggtgtcct cttcattgct cactgttcgg     600
gctgccatcc ccattatcat gggggccaac attggaacgt caatcaccaa cactattgtt     660
gcgctcatgc aggtgggaga tcggagtgag ttcagaagag cttttgcagg agccactgtc     720
catgacttct tcaactggct gtccgtgttg gtgctcttgc ccgtggaggt ggccacccat     780
tacctcgaga tcataaccca gcttatagtg gagagcttcc acttcaagaa tggagaagat     840
gccccagatc ttctgaaagt catcactaag cccttcacaa agctcattgt ccagctggat     900 aaaaagtta tcagccaaat tgcaatgaac gatgaaaaag cgaaaaacaa gagtcttgtc     960
aagatttggt gcaaaacttt taccaacaag acccagatta acgtcactgt tccctcgact    1020
gctaactgca cctcccttc cctctgttgg acggatggca tccaaaactg gaccatgaag    1080
aatgtgacct acaaggagaa catcgccaaa tgccagcata tctttgtgaa tttccacctc    1140
```

-continued

```
ccggatcttg ctgtgggcac catcttgctc atactctccc tgctggtcct ctgtggttgc    1200
ctgatcatga ttgtcaagat cctgggctct gtgctcaagg ggcaggtcgc cactgtcatc    1260
aagaagacca tcaacactga tttccccttt ccctttgcat ggttgactgg ctacctggcc    1320
atcctcgtcg gggcaggcat gaccttcatc gtacagagca gctctgtgtt cacgtcggcc    1380 ttgaccccc tgattggaat cggcgtgata accattgaga gggcttatcc actcacgctg     1440
ggctccaaca tcggcaccac caccaccgcc atcctggccg ccttagccag ccctggcaat    1500
gcattgagga gttcactcca gatcgccctg tgccacttt tcttcaacat ctccggcatc     1560
ttgctgtggt acccgatccc gttcactcgc ctgcccatcc gcatggccaa ggggctgggc    1620
aacatctctg ccaagtatcg ctggttcgcc gtcttctacc tgatcatctt cttcttcctg    1680
atcccgctga cggtgtttgg cctctcgctg gccggctggc gggtgctggt tggtgtcggg    1740
gttcccgtcg tcttcatcat catcctggta ctgtgcctcc gactcctgca gtctcgctgc    1800
ccacgcgtcc tgccgaagaa actccagaac tggaacttcc tgccgctgtg gatgcgctcg    1860
ctgaagccct gggatgccgt cgtctccaag ttcaccggct gcttccagat gcgctgctgc    1920
tactgctgcc gcgtgtgctg ccgcgcgtgc tgcttgctgt gtggctgccc caagtgctgc    1980
cgctgcagca gtgctgcgca ggacttggag gaggcgcagg aggggcagga tgtccctgtc    2040
aaggctcctg agacctttga taacataacc attagcagag aggctcaggg tgaggtccct    2100
gcctcggact caaagaccga atgcacggcc ttgtagggga cgccccagat tgtcagggat    2160 gggggatgg tccttgagtt ttgcatgctc tcctccctcc cacttctgca ccctttcacc     2220
acctcgagga gatttgctcc ccattagcga atgaaattga tgcagtccta aaaaaaaaa    2280 aaaaaaaa                                                            2288
```

<210> SEQ ID NO 2
<211> LENGTH: 690
<212> TYPE: PRT
<213> ORGANISM: HOMO SAPIENS

<400> SEQUENCE: 2

```
Met Ala Pro Trp Pro Glu Leu Gly Asp Ala Gln Pro Asn Pro Asp Lys
  1               5                  10                  15

Tyr Leu Glu Gly Ala Ala Gly Gln Gln Pro Thr Ala Pro Asp Lys Ser
             20                  25                  30

Lys Glu Thr Asn Lys Thr Asp Asn Thr Glu Ala Pro Val Thr Lys Ile
         35                  40                  45

Glu Leu Leu Pro Ser Tyr Ser Thr Ala Thr Leu Ile Asp Glu Pro Thr
     50                  55                  60

Glu Val Asp Asp Pro Trp Asn Leu Pro Thr Leu Gln Asp Ser Gly Ile
 65                  70                  75                  80

Lys Trp Ser Glu Arg Asp Thr Lys Gly Lys Ile Leu Cys Phe Phe Gln
                 85                  90                  95

Gly Ile Gly Arg Leu Ile Leu Leu Gly Phe Leu Tyr Phe Phe Val
                100                 105                 110

Cys Ser Leu Asp Ile Leu Ser Ser Ala Phe Gln Leu Val Gly Gly Lys
            115                 120                 125

Met Ala Gly Gln Phe Phe Ser Asn Ser Ser Ile Met Ser Asn Pro Leu
        130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
```

-continued

```
                165                 170                 175
Thr Val Arg Ala Ala Ile Pro Ile Ile Met Gly Ala Asn Ile Gly Thr
                    180                 185                 190
Ser Ile Thr Asn Thr Ile Val Ala Leu Met Gln Val Gly Asp Arg Ser
                195                 200                 205
Glu Phe Arg Arg Ala Phe Ala Gly Ala Thr Val His Asp Phe Phe Asn
            210                 215                 220
Trp Leu Ser Val Leu Val Leu Pro Val Glu Val Ala Thr His Tyr
225                 230                 235                 240
Leu Glu Ile Ile Thr Gln Leu Ile Val Glu Ser Phe His Phe Lys Asn
                    245                 250                 255
Gly Glu Asp Ala Pro Asp Leu Leu Lys Val Ile Thr Lys Pro Phe Thr
                260                 265                 270
Lys Leu Ile Val Gln Leu Asp Lys Lys Val Ile Ser Gln Ile Ala Met
                275                 280                 285
Asn Asp Glu Lys Ala Lys Asn Lys Ser Leu Val Lys Ile Trp Cys Lys
            290                 295                 300
Thr Phe Thr Asn Lys Thr Gln Ile Asn Val Thr Val Pro Ser Thr Ala
305                 310                 315                 320
Asn Cys Thr Ser Pro Ser Leu Cys Trp Thr Asp Gly Ile Gln Asn Trp
                    325                 330                 335
Thr Met Lys Asn Val Thr Tyr Lys Glu Asn Ile Ala Lys Cys Gln His
                340                 345                 350
Ile Phe Val Asn Phe His Leu Pro Asp Leu Ala Val Gly Thr Ile Leu
                355                 360                 365
Leu Ile Leu Ser Leu Leu Val Leu Cys Gly Cys Leu Ile Met Ile Val
370                 375                 380
Lys Ile Leu Gly Ser Val Leu Lys Gly Gln Val Ala Thr Val Ile Lys
385                 390                 395                 400
Lys Thr Ile Asn Thr Asp Phe Pro Phe Pro Phe Ala Trp Leu Thr Gly
                    405                 410                 415
Tyr Leu Ala Ile Leu Val Gly Ala Gly Met Thr Phe Ile Val Gln Ser
                420                 425                 430
Ser Ser Val Phe Thr Ser Ala Leu Thr Pro Leu Ile Gly Ile Gly Val
                435                 440                 445
Ile Thr Ile Glu Arg Ala Tyr Pro Leu Thr Leu Gly Ser Asn Ile Gly
    450                 455                 460
Thr Thr Thr Thr Ala Ile Leu Ala Ala Leu Ala Ser Pro Gly Asn Ala
465                 470                 475                 480
Leu Arg Ser Ser Leu Gln Ile Ala Leu Cys His Phe Phe Asn Ile
                    485                 490                 495
Ser Gly Ile Leu Leu Trp Tyr Pro Ile Pro Phe Thr Arg Leu Pro Ile
            500                 505                 510
Arg Met Ala Lys Gly Leu Gly Asn Ile Ser Ala Lys Tyr Arg Trp Phe
            515                 520                 525
Ala Val Phe Tyr Leu Ile Ile Phe Phe Leu Ile Pro Leu Thr Val
                530                 535                 540
Phe Gly Leu Ser Leu Ala Gly Trp Arg Val Leu Val Gly Val Gly Val
545                 550                 555                 560
Pro Val Val Phe Ile Ile Ile Leu Val Leu Cys Leu Arg Leu Leu Gln
                    565                 570                 575
Ser Arg Cys Pro Arg Val Leu Pro Lys Lys Leu Gln Asn Trp Asn Phe
                580                 585                 590
```

Leu Pro Leu Trp Met Arg Ser Leu Lys Pro Trp Asp Ala Val Val Ser
        595                 600                 605

Lys Phe Thr Gly Cys Phe Gln Met Arg Cys Cys Tyr Cys Cys Arg Val
        610                 615                 620

Cys Cys Arg Ala Cys Cys Leu Cys Gly Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
            660                 665                 670

Glu Ala Gln Gly Glu Val Pro Ala Ser Asp Ser Lys Thr Glu Cys Thr
        675                 680                 685

Ala Leu
    690

<210> SEQ ID NO 3
<211> LENGTH: 621
<212> TYPE: DNA
<213> ORGANISM: HOMO SAPIENS

<400> SEQUENCE: 3
gaattcggct tgccaccaac gagttcatcc tgagcctgct ggtcctctgt ggttgcctga      60
tcatgattgt caagatcctg ggctctgtgc taaggggcag gtcgccactg tcatcaagaa     120
gaccatcaac actgatttcc cctttccctt tgcatggttg actggctacc tggccatcct     180
cgtcggggca ggcatgacct tcatcgtaca gagcagctct gtgttcacgt cggccttgac     240 cccctgatt ggaatcggcg tgataaccat tgagagggct atccactca cgctgggctc      300 caacatcggc accaccacca ccgccatcct ggccgcctta gccagccctg gcaatgcatt     360
gaggagttca ctccagatcg ccctgtgcca ctttttcttc aacatctccg gcatcttgct     420
gtggtacccg atcccgttca ctcgcctgcc catccgcatg ccaaggggc tgggcaacat      480 ctctgccaag tatcgctggt tcgccgtctt ctacctgatc atcttcttct tcctgatccc     540
gctgacggtg tttgccctct gctggttgcc tctctacaag ccgaattctg cagatatcca     600
tcacactggc ggccgctcga g                                              621

<210> SEQ ID NO 4
<211> LENGTH: 155
<212> TYPE: PRT
<213> ORGANISM: HOMO SAPIENS
<220> FEATURE:
<221> NAME/KEY: UNSURE
<222> LOCATION: (19)(22)

<400> SEQUENCE: 4

Lys Lys Thr Ile Asn Thr Asp Phe Pro Phe Pro Phe Ala Trp Leu Thr
  1               5                  10                  15

Gly Tyr Xaa Ala Ile Xaa Val Gly Ala Gly Met Thr Phe Ile Val Gln
            20                  25                  30

Ser Ser Val Phe Thr Ser Ala Leu Thr Pro Leu Ile Gly Ile Gly
        35                  40                  45

Val Ile Thr Ile Glu Arg Ala Tyr Pro Leu Thr Leu Gly Ser Asn Ile
    50                  55                  60

Gly Thr Thr Thr Thr Ala Ile Leu Ala Ala Leu Ala Ser Pro Gly Asn
65                  70                  75                  80

Ala Leu Arg Ser Ser Leu Gln Ile Ala Leu Cys His Phe Phe Phe Asn

-continued

```
                85                  90                  95
Ile Ser Gly Ile Leu Leu Trp Tyr Pro Ile Pro Phe Thr Arg Leu Pro
            100                 105                 110

Ile Arg Met Ala Lys Gly Leu Gly Asn Ile Ser Ala Lys Tyr Arg Trp
        115                 120                 125

Phe Ala Val Phe Tyr Leu Ile Ile Phe Phe Phe Leu Ile Pro Leu Thr
    130                 135                 140

Val Phe Ala Leu Cys Trp Leu Pro Leu Tyr Lys
145                 150                 155
```

HUMAN SODIUM DEPENDENT PHOSPHATE TRANSPORTER (IPT-1)

This application is a division of application Ser. No. 08/935,433, filed Sep. 23, 1997, which claims the benefit of U.S. Provisional Application No. 60/044,974 filed Apr. 28, 1997, both of whose contents are incorporated herein by reference in their entireties.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to the sodium dependent phosphate transporters family, hereinafter referred to as IPT-1. The invention also relates to inhibiting or activating the action of such polynucleotides and polypeptides.

BACKGROUND OF THE INVENTION

Phosphate retention has been shown to play a critical role in the development of uremic bone disease. Blockade of intestinal absorption of phosphate could provide an important target for prevention of uremic bone disease in patients who have end stage renal disease (ESRD) and possibly a target for slowing the progression of renal disease itself. Patients with ESRD cannot excrete phosphate, and they develop hyperphosphatemia, secondary hyperparathyroidism and uremic bone disease. Current treatment of these patients involves dietary phosphate restriction and phosphate binders, both of which have severe drawbacks. Blockade of phosphate absorption with a specific inhibitor of the intestinal phosphate transporter would provide a major advance in the treatment of these patients. This indicates that the sodium dependent phosphate transporters family has an established, proven history as therapeutic targets. Clearly there is a need for identification and characterization of further members of the sodium dependent phosphate transporters family which can play a role in preventing, ameliorating or correcting dysfunctions or diseases, including, but not limited to, chronic renal failure, end stage renal disease, uremic bone disease, and cancer.

SUMMARY OF THE INVENTION

In one aspect, the invention relates to IPT-1 polypeptides and recombinant materials and methods for their production. Another aspect of the invention relates to methods for using such IPT-1 polypeptides and polynucleotides. Such uses include the treatment of chronic renal failure, end stage renal disease, uremic bone disease, and cancer, among others. In still another aspect, the invention relates to methods to identify agonists and antagonists using the materials provided by the invention, and treating conditions associated with IPT-1 imbalance with the identified compounds. Yet another aspect of the invention relates to diagnostic assays for detecting diseases associated with inappropriate IPT-1 activity or levels.

DESCRIPTION OF THE INVENTION

Definitions

The following definitions are provided to facilitate understanding of certain terms used frequently herein.

"IPT-1" refers, among others, generally to a polypeptide having the amino acid sequence set forth in SEQ ID NO:2 or an allelic variant thereof.

"IPT-1 activity or IPT-1 polypeptide activity" or "biological activity of the IPT-1 or IPT-1 polypeptide" refers to the metabolic or physiologic function of said IPT-1 including similar activities or improved activities or these activities with decreased undesirable side-effects. Also included are antigenic and immunogenic activities of said IPT-1.

"IPT-1 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to IPT-1 polypeptides (or IPT-1 proteins) The IPT-1 polypeptides include the polypeptide of SEQ ID NOS:2 and 4; as well as polypeptides comprising the amino acid sequence of SEQ ID NO: 2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within IPT-1 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably IPT-1 polypeptide exhibit at least one biological activity of IPT-1.

The IPT-1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the IPT-1 polypeptides are also included in the invention. A fragment is a polypeptide having an amino acid sequence that entirely is the same as part, but not all, of the amino acid sequence of the aforementioned IPT-1 polypeptides. As with IPT-1 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of IPT-1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of IPT-1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate IPT-1 activity, including those with a similar activity or an improved activity, or with a decreased undesirable activity. Also included are those that are antigenic or immunogenic in an animal, especially in a human.

Preferably, all of these polypeptide fragments retain the biological activity of the IPT-1, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The IPT-1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to IPT-1 polynucleotides. IPT-1 polynucleotides include isolated polynucleotides which encode the IPT-1 polypeptides and fragments, and polynucleotides closely related thereto. More specifically, IPT-1 polynucleotide of the invention include a polynucleotide comprising the nucleotide sequence contained in SEQ ID NO:1 encoding a IPT-1 polypeptide of SEQ ID NO: 2, and polynucleotides having the particular sequences of SEQ ID NOS:1 and 3. IPT-1 polynucleotides further include a polynucleotide comprising a nucleotide sequence that has at least 80% identity over its entire length to a nucleotide sequence encoding the IPT-1 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under IPT-1 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such IPT-1 polynucleotides.

IPT-1 of the invention is structurally related to other proteins of the sodium dependent phosphate transporters family, as shown by the results of sequencing the cDNA encoding human IPT-1. The cDNA sequence of SEQ ID NO:1 contains an open reading frame (nucleotide number 64 to 2136) encoding a polypeptide of 691 amino acids of SEQ ID NO:2. The amino acid sequence of Table 1 (SEQ ID NO:2) has about 76 identity (using FASTA) in 691 amino acid residues with bovine sodium dependent phosphate transporter, X81699, (Helps et al. Eur. J. Biochem. 228:927–930. 1995). Furthermore, IPT-1 is 55% identical to human NaPi-3 over 625 amino acids (Magagnin et al. PNAS 905979–5983, 1993). The nucleotide sequence of Table 1 (SEQ ID NO:1) has about 78% identity (using FASTA) in 2242 nucleotide residues with bovine sodium dependent phosphate transporter, X81699, (Helps et al. Eur. J. Biochem. 228:927–930, 1995). Furthermore, IPT-1 is 58% identical to human NaPi-3 over 2270 nucleotides (Magagnin et al. PNAS 905979–5983, 1993). Thus, IPT-1 polypeptides and polynucleotides of the present invention are expected to have, inter alia, similar biological functions/properties to their homologous polypeptides and polynucleotides, and their utility is obvious to anyone skilled in the art.

TABLE 1[a]

```
CGGGCCAGGTTTCCAGGCTCGGCCGCCGCCTCCATCCCAGCACCTGCGGAGGGAGCGCTG
ACCATGGCTCCCTGGCCTGAATTGGGAGATGCCCAGCCCAACCCCGATAAGTACCTCGAA
GGGGCCGCAGGTCAGCAGCCCACTGCCCCTGATAAAAGCAAAGAGACCAACAAAACAGAT
AACACTGAGGCACCTGTAACCAAGATTGAACTTCTGCCGTCCTACTCCACGGCTACACTG
ATAGATGAGCCCACTGAGGTGGATGACCCCTGGAACCTACCCACTCTTCAGGACTCGGGG
ATCAAGTGGTCAGAGAGAGACACCAAAGGGAAGATTCTCTGTTTCTTCCAAGGGATTGGG
AGATTGATTTTACTTCTCGGATTTCTCTACTTTTTCGTGTGCTCCCTGGATATTCTTAGT
AGCGCCTTCCAGCTGGTTGGAGGAAAAATGGCAGGACAGTTCTTCAGCAACAGCTCTATT
ATGTCCAACCCTTTGTTGGGGCTGGTGATCGGGGTGCTGGTGACCGTCTTGGTGCAGAGC
TCCAGCACCTCAACGTCCATCGTTGTCAGCATGGTGTCCTCTTCATTGCTCACTGTTCGG
GCTGCCATCCCCATTATCATGGGGGCCAACATTGGAACGTCAATCACCAACACTATTGTT
GCGCTCATGCAGGTGGGAGATCGGAGTGAGTTCAGAAGAGCTTTTGCAGGAGCCACTGTC
CATGACTTCTTCAACTGGCTGTCCGTGTTGGTGCTCTTGCCCGTGGAGGTGGCCACCCAT
TACCTCGAGATCATAACCCAGCTTATAGTGGAGAGCTTCCACTTCAAGAATGGAGAAGAT
GCCCCAGATCTTCTGAAAGTCATCACTAAGCCCTTCACAAAGCTCATTGTCCAGCTGGAT
AAAAAAGTTATCAGCCAAATTGCAATGAACGATGAAAAAGCGAAAAACAAGAGTCTTGTC
AAGATTTGGTGCAAAACTTTTACCAACAAGACCCAGATTAACGTCACTGTTCCCTCGACT
GCTAACTGCACCTCCCCTTCCCTCTGTTGGACGGATGGCATCCAAAACTGGACCATGAAG
AATGTGACCTACAAGGAGAACATCGCCAAATGCCAGCATATCTTTGTGAATTTCCACCTC
CCGGATCTTGCTGTGGGCACCATCTTGCTCATACTCTCCCTGCTGGTCCTCTGTGGTTGC
CTGATCATGATTGTCAAGATCCTGGGCTCTGTGCTCAAGGGGCAGGTCGCCACTGTCATC
AAGAAGACCATCAACACTGATTTCCCCTTTCCCTTTGCATGGTTGACTGGCTACCTGGCC
ATCCTCGTCGGGGCAGGCATGACCTTCATCGTACAGAGCAGCTCTGTGTTCACGTCGGCC
TTGACCCCCCTGATTGGAATCGGCGTGATAACCATTGAGAGGGCTTATCCACTCACGCTG
GGCTCCAACATCGGCACCACCACCACCGCCATCCTGGCCGCCTTAGCCAGCCCTGGCAAT
GCATTGAGGAGTTCACTCCAGATCGCCCTGTGCCACTTTTTCTTCAACATCTCCGGCATC
TTGCTGTGGTACCCGATCCCGTTCACTCGCCTGCCCATCCGCATGGCCAAGGGGCTGGGC
AACATCTCTGCCAAGTATCGCTGGTTCGCCGTCTTCTACCTGATCATCTTCTTCTTCCTG
ATCCCGCTGACGGTGTTTGGCCTCTCGCTGGCCGGCTGGCGGGTGCTGGTTGGTGTCGGG
GTTCCCGTCGTCTTCATCATCATCCTGGTACTGTGCCTCCGACTCCTGCAGTCTCGCTGC
CCACGCGTCCTGCCGAAGAAACTCCAGAACTGGAACTTCCTGCCGCTGTGGATGCGCTCG
CTGAAGCCCTGGGATGCCGTCGTCTCCAAGTTCACCGGCTGCTTCCAGATGCGCTGCTGC
TACTGCTGCCGCGTGTGCTGCCGCGCGTGCTGCTTGCTGTGTGGCTGCCCCAAGTGCTGC
CGCTGCAGCAAGTGCTGCGAGGACTTGGAGGAGGCGCAGGAGGGGCAGGATGTCCCTGTC
AAGGCTCCTGAGACCTTTGATAACATAACCATTAGCAGAGAGGCTCAGGGTGAGGTCCCT
GCCTCGGACTCAAAGACCGAATGCACGGCCTTGTAGGGGACGCCCCAGATTGTCAGGGAT
GGGGGGATGGTCCTTGAGTTTTGCATGCTCTCCTCCCTCCCACTTCTGCACCCTTTCACC
ACCTCGAGGAGATTTGCTCCCCATTAGCGAATGAAATTGATGCAGTCCTAAAAAAAAAAA
AAAAA
```

[a] A nucleotide sequence of a human IPT-1 (SEQ ID NO: 1).

TABLE 2[b]

MAPWPELGDAQPNPDKYLEGAAGQQPTAPDKSKETNKTDNTEAPVTKIELLPSYSTATLI

DEPTEVDDPWNLPTLQDSGIKWSERDTKGKILCFFQGIGRLILLLGFLYFFVCSLDILSS

AFQLVGGKMAGQFFSNSSIMSNPLLGLVIGVLVVVLVQSSSTSTSIVVSMVSSSLLTVRA

AIPIIMGANIGTSITNTIVALMQVGDRSEFRRAFAGATVHDFFNWLSVLVLLPVEVATHY

LEIITQLIVESFHFKNGEDAPDLLKVITKPFTKLIVQLDKKVISQIAMNDEKAKNKSLVK

IWCKTFTNKTQINVTVPSTANCTSPSLCWTDGIQNWTMKNVTYKENIAKCQHIFVNFHLP

DLAVGTILLILSLLVLCGCLIMIVKILGSVLKGQVATVIKKTINTDFPFPFAWLTGYLAI

LVGAGMTFIVQSSSVFTSALTPLIGIGVITIERAYPLTLGSNIGTTTTAILAALASPGNA

LRSSLQIALCHFFFNISGILLWYPIPFTRLPIRMAKGLGNISAKYRWFAVFYLIIFFFLI

PLTVFGLSLAGWRVLVGVGVPVVFIIILVLCLRLLQSRCPRVLPKKLQNWNFLPLWMRSL

KPWDAVVSKFTGCFQMRCCYCCRVCCRACCLLCGCPKCCRCSKCCEDLEEAQEGQDVPVK

APETFDNITISREAQGEVPASDSKTECTAL

[b]An amino acid sequence of a human IPT-1 (SEQ ID NQ: 2).

One polynucleotide of the present invention encoding IPT-1 may be obtained using standard cloning and screening, from a cDNA library derived from mRNA in cells of human small intestine and lung using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding IPT-1 polypeptide of SEQ ID NO:2 may be identical to the polypeptide encoding sequence contained in Table 1 (nucleotide number 64 to 2136 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of IPT-1 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding IPT-1 variants comprising the amino acid sequence of IPT-1 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3[c]

GAATTCGGCTTGCCACCAACGAGTTCATCCTGAGCCTGCTGGTCCTCTGTGGTTGCCTGA

TCATGATTGTCAAGATCCTGGGCTCTGTGCTAAGGGGCAGGTCGCCACTGTCATCAAGAA

GACCATCAACACTGATTTCCCCTTTCCCTTTGCATGGTTGACTGGCTACCTGGCCATCCT

CGTCGGGGCAGGCATGACCTTCATCGTACAGAGCAGCTCTGTGTTCACGTCGGCCTTGAC

CCCCCTGATTGGAATCGGCGTGATAACCATTGAGAGGGCTTATCCACTCACGCTGGGCTC

CAACATCGGCACCACCACCACCGCCATCCTGGCCGCCTTAGCCAGCCCTGGCAATGCATT

GAGGAGTTCACTCCAGATCGCCCTGTGCCACTTTTTCTTCAACATCTCCGGCATCTTGCT

GTGGTACCCGATCCCGTTCACTCGCCTGCCCATCCGCATGGCCAAGGGGCTGGGCAACAT

CTCTGCCAAGTATCGCTGGTTCGCCGTCTTCTACCTGATCATCTTCTTCTTCCTGATCCC

TABLE 3<sup>c</sup>-continued

GCTGACGGTGTTTGCCCTCTGCTGGTTGCCTCTCTACAAGCCGAATTCTGCAGATATCCA

TCACACTGGCGGCCGCTCGAG

<sup>c</sup>A partial nucleotide sequence of a human IPT-1 (SEQ ID NO: 3).

TABLE 4<sup>d</sup>

KKTINTDFPFPFAWLTGYXAIXVGAGMTFIVQSSSVFTSALTPLIGIGVITIERAYPLTL

GSNIGTTTTAILAALASPGNALRSSLQIALCHFFFNISGILLWYPIPFTRLPIRMAKGLG

NISAKYRWFAVFYLIIFFFLIPLTVFALCWLPLYK

<sup>d</sup>A partial amino acid sequence of a human IPT-1 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficient identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding IPT-1 polypeptide and to isolate cDNA and genomic clones of other genes (including genes encoding homologs and orthologs from species other than human) that have a high sequence similarity to the IPT-1 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding IPT-1 polypeptide, including homologs and orthologs from species other than human, comprises the steps of screening an appropriate library under stringent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Thus in another aspect, IPT-1 polynucleotides of the present invention further include a nucleotide sequence comprising a nucleotide sequence that hybridize under stringent condition to a nucleotide sequence having SEQ ID NO: 1 or a fragment thereof (including that of SEQ ID NO:3). Also included with IPT-1 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs denyed from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplamic space or into the extracellular environment, appropriate secretion signals may be incorporated into the desired polypeptide. These signals may be endogenous to the polypeptide or they may be heterologous signals.

If the IPT-1 polypeptide is to be expressed for use in screening assays, generally, it is preferred that the polypeptide be produced at the surface of the cell. In this event, the cells may be harvested prior to use in the screening assay. If IPT-1 polypeptide is secreted into the medium, the medium can be recovered in order to recover and purify the polypeptide; if produced intracellularly, the cells must first be lysed before the polypeptide is recovered. IPT-1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of IPT-1 polynucleotides for use as diagnostic reagents. Detection of a mutated form of IPT-1 gene associated with a dysfunction will provide a diagnostic tool that can add to or define a diagnosis of a disease or susceptibility to a disease which results from under-expression, over-expression or altered expression of IPT-1. Individuals carrying mutations in the IPT-1 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IPT-1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturig agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al, *Proc Natl Acad Sci USA* (1985) 85: 4397–4401. In another embodiment, an array of oligonucleotides probes comprising IPT-1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to chronic renal failure, end stage renal disease, uremic bone disease, and cancer, through detection of mutation in the IPT-1 gene by the methods described.

In addition, chronic renal failure, end stage renal disease, uremic bone disease, and cancer can be diagnosed by methods comprising determining from a sample derived from a subject an abnormally decreased or increased level of IPT-1 polypeptide or IPT-1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an IPT-1 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly chronic renal failure, end stage renal disease, uremic bone disease, and cancer, which comprises:

(a) a IPT-1 polynucleotide, preferably the nucleotide sequence of SEQ ID NO: 1, or a fragment thereof;
(b) a nucleotide sequence complementary to that of (a);
(c) a IPT-1 polypeptide, preferably the polypeptide of SEQ ID NO: 2, or a fragment thereof; or
(d) an antibody to a IPT-1 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the IPT-1 polypeptides. The term "immunospecific" means that the antibodies have substantial greater affinity for the polypeptides of the invention than their affinity for other related polypeptides in the prior art.

Antibodies generated against the IPT-1 polypeptides can be obtained by administering the polypeptides or epitope-bearing fragments, analogs or cells to an animal preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTI-BODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above described antibodies may be employed to isolate or to identify clones expressing the polypeptide or to purify the polypeptides by affinity chromatography.

Antibodies against IPT-1 polypeptides may also be employed to treat chronic renal failure, end stage renal disease, uremic bone disease, and cancer, among others.

Vaccines

Another aspect of the invention relates to a method for inducing an immunological response in a mammal which comprises inoculating the mammal with IPT-1 polypeptide, or a fragment thereof, adequate to produce antibody and/or T cell immune response to protect said animal from chronic renal failure, end stage renal disease, uremic bone disease, and cancer, among others. Yet another aspect of the invention relates to a method of inducing immunological response in a mammal which comprises, delivering IPT-1 polypeptide via a vector directing expression of IPT-1 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a IPT-1 polypeptide wherein the composition comprises a IPT-1 polypeptide or IPT-1 gene. The vaccine formulation may further comprise a suitable carrier. Since IPT-1 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The IPT-1 polypeptide of the present invention may be employed in a screening process for compounds which activate (agonists) or inhibit activation of (antagonists, or otherwise called inhibitors) the IPT-1 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., *Current Protocols in Immunology* 1(2): Chapter 5 (1991).

IPT-1 polypeptides are responsible for many biological functions, including many pathologies. Accordingly, it is desirous to find compounds and drugs which stimulate IPT-1 polypeptide on the one hand and which can inhibit the function of IPT-1 polypeptide on the other hand. In general, agonists are employed for therapeutic and prophylactic purposes for such conditions as chronic renal failure, end stage renal disease, uremic bone disease, and cancer. Antagonists may be employed for a variety of therapeutic and prophylactic purposes for such conditions as chronic renal failure, end stage renal disease, uremic bone disease, and cancer.

In general, such screening procedures may involve using appropriate cells which express the IPT-1 polypeptide or respond to IPT-1 polypeptide of the present invention. Such cells include cells from mammals, yeast, Drosophila or *E. coli*. Cells which express the IPT-1 polypeptide (or cell membrane containing the expressed polypeptide) or respond to IPT-1 polypeptide are then contacted with a test compound to observe binding, or simulation or inhibition of a functional response. The ability of the cells which were contacted with the candidate compounds is compared with the same cells which were not contacted for IPT-1 activity.

Cell lines (transient or stable) expressing the recombinant protein are useful for establishing screening assays and for characterization of the protein. Phosphate uptake assays using these cells would be useful in the identification of inhibitors of phosphate transport. These assays could be either whole cell based or membrane based.

The assays may simply test binding of a candidate compound wherein adherence to the cells bearing the IPT-1 polypeptide is detected by means of a label directly or indirectly associated with the candidate compound or in an assay involving competition with a labeled competitor. Further, these assays may test whether the candidate compound results in a signal generated by activation of the IPT-1 polypeptide, using detection systems appropriate to the cells bearing the IPT-1 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a IPT-1 polypeptide to form a mixture, measuring IPT-1 activity in the mixture, and comparing the IPT-1 activity of the mixture to a standard.

The IPT-1 cDNA, protein and antibodies to the protein may also be used to configure assays for detecting the effect of added compounds on the production of IPT-1 mRNA and protein in cells. For example, an ELISA may be constructed for measuring secreted or cell associated levels of IPT-1 protein using monoclonal and polyclonal antibodies by standard methods known in the art, and this can be used to discover agents which may inhibit or enhance the production of IPT-1 (also called antagonist or agonist respectively) from suitably manipulated cells or tissues.

The IPT-1 protein may be used to identify membrane bound or soluble receptors, if any, through standard receptor binding techniques known in the art. These include, but are not limited to, ligand binding and crosslinking assays in which the IPT-1 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of IPT-1 which compete with the binding of IPT-1 to its receptors, if any. Standard methods for conducting screening assays are well understood in the art.

Examples of potential IPT-1 polypeptide antagonists include antibodies or, in some cases, oligonucleotides or proteins which are closely related to the ligands, substrates, enzymes, receptors, etc., as the case may be, of the IPT-1 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for IPT-1 polypeptides; or compounds which decrease or enhance the production of IPT-1 polypeptides, which comprises:

(a) a IPT-1 polypeptide, preferably that of SEQ ID NO:2;
(b) a recombinant cell expressing a IPT-1 polypeptide, preferably that of SEQ ID NO:2;
(c) a cell membrane expressing a IPT-1 polypeptide; preferably that of SEQ ID NO: 2; or
(d) antibody to a IPT-1 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating abnormal conditions such as, chronic renal failure, end stage renal disease, uremic bone disease, and cancer, related to both an excess of and insufficient amounts of IPT-1 polypeptide activity.

If the activity of IPT-1 polypeptide is in excess, several approaches are available. One approach comprises administering to a subject an inhibitor compound (antagonist) as hereinabove described along with a pharmaceutically acceptable carrier in an amount effective to inhibit the function of the IPT-1 polypeptide, such as, for example, by blocking the binding of ligands, substrates, enzymes, receptors, etc., or by inhibiting a second signal, and thereby alleviating the abnormal condition. In another approach, soluble forms of IPT-1 polypeptides still capable of binding the ligand, substrate, enzymes, receptors, etc. in competition with endogenous IPT-1 polypeptide may be administered. Typical embodiments of such competitors comprise fragments of the IPT-1 polypeptide.

In another approach, soluble forms of IPT-1 polypeptides still capable of binding the ligand in competition with endogenous IPT-1 polypeptide may be administered. Typical embodiments of such competitors comprise fragments of the IPT-1 polypeptide.

In still another approach, expression of the gene encoding endogenous IPT-1 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of IPT-1 and its activity, several approaches are also available. One approach comprises administering to a subject a therapeutically effective amount of a compound which activates IPT-1 polypeptide, i.e., an agonist as described above, in combination with a pharmaceutically acceptable carrier, to thereby alleviate the abnormal condition. Alternatively, gene therapy may be employed to effect the endogenous production of IPT-1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of IPT-1 polypeptides in combination with a suitable pharmaceutical carrier.

Formulation and Administration

Peptides, such as the soluble form of IPT-1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

This cDNA sequence can be expressed in heterologous systems (prokaryotic or eukaryotic) to allow high level protein expression and production. Recombinant protein produced in, and purified from, these systems is useful in screening assays to identify inhibitors of catalytic activity as well as a source of material for structural studies and antibody production. Cell lines (transient or stable) expressing the recombinant protein are useful for establishing screening assays and for characterization of the protein.

All publications, including but not limited to patents and patent applications, cited in this specification are herein incorporated by reference as if each individual publication were specifically and individually indicated to be incorporated by reference herein as though fully set forth.

What is claimed is:

1. An isolated polypeptide comprising the amino acid sequence set forth in SEQ ID NO:2.

2. The isolated polypeptide of claim 1 consisting of the amino acid sequence set forth in SEQ ID NO:2.

* * * * *